(12) United States Patent
Neyses

(10) Patent No.: US 8,013,009 B2
(45) Date of Patent: Sep. 6, 2011

(54) METHODS OF DIAGNOSING INFERTILITY BY DETECTING PMCA4 MUTATIONS

(76) Inventor: Ludwig Neyses, Manchester (GB)

( * ) Notice: Subject to any disclaimer, the term of this patent is extended or adjusted under 35 U.S.C. 154(b) by 1072 days.

(21) Appl. No.: 10/563,193

(22) PCT Filed: Jul. 1, 2004

(86) PCT No.: PCT/EP2004/007168
§ 371 (c)(1),
(2), (4) Date: Jan. 3, 2006

(87) PCT Pub. No.: WO2005/002495
PCT Pub. Date: Jan. 13, 2005

(65) Prior Publication Data
US 2006/0276529 A1    Dec. 7, 2006

(30) Foreign Application Priority Data

Jul. 3, 2003 (DE) .................................. 103 30 213

(51) Int. Cl.
*A01N 43/36* (2006.01)
*A61K 31/40* (2006.01)
*G01N 33/567* (2006.01)
(52) U.S. Cl. ...................... 514/425; 435/7.21; 435/806
(58) Field of Classification Search .................. 514/425; 435/7.21, 806
See application file for complete search history.

(56) References Cited

U.S. PATENT DOCUMENTS

| 4,066,757 | A | * | 1/1978 | Pasquale | 514/177 |
| 5,314,447 | A | * | 5/1994 | Papurt | 128/842 |
| 2002/0164368 | A1 | * | 11/2002 | Zimmerman | 424/452 |

FOREIGN PATENT DOCUMENTS

EP    0 552 108 A2    7/1993

OTHER PUBLICATIONS

Chaudhary et al. Am. J. Physiol Cell Physiol. 2001, vol. 280, pp. C1027-C1030.*
Wennemuth et al. J. Gen. Physiol. Jun. 30, 2003, vol. 122, pp. 115-128.*
Perloe et al. The formula of Male Fertility. Published online Feb. 2002, pp. 1-9.*
Burnett et al. Toxicology, 1997, vol. 119, pp. 83-93.*
Schuh Kai et al : "Plasma membrane Ca2+ ATPase 4 is required for sperm motility and male fertility" Journal of Biological Chemistry, vol. 279, No. 27, Jul. 2, 2004, pp. 28220-28226, XP008036550 ISSN : 0021-9258.
Kanwar U et al : "Gossypol Inhibition of CA++ Uptake and CA++-Atpase in Human Ejaculated Spermatozoal Plasma Membrane Vesicles" Contraception, Geron-X, Inc., Los Altos, CA, US, vol. 39, No. 4, Apr. 1, 1989, pp. 431-445, XP000561575 ISSN : 0010-7824.
Breitbart H et al : "The Role of Calcium and CA2+-Atpase in Maintaining Motility in Ram Spermatozoa" Journal of Biological Chemistry . (Microfilms), American Society of Biological Chemists, Baltimore, MD, US, vol. 260, No. 21, Sep. 25, 1985, pp. 11548-11553, XP001009929.
Patni Anil K et al : "Role of intracellular calcium in the spermicidal action of 2',4'-dichlorobenzamil, a novel contact spermicide" Journal of Pharmacy and Pharmacology, vol. 53, No. 10, Oct. 2001, pp. 1387-1392, XP008036557 ISSN : 0022-3573.
Schuh Kai et al : "The sarcolemmal calcium pump PMCA : An effector of platelet aggregation ." Circulation, vol. 106, No. 19 Supplement, Nov. 5, 2002, pp. 11-79, XP008036566 & Abstracts From Scientific Sessions ; Chicago, IL, USA ; Nov. 17-20, 2002 ISSN : 0009-7322.
Yang Z et al : "Na+-Ca2+ exchange activity is localized in the T-tubules of rat ventricular myocytes" Circulation Research, vol. 91, No. 4, Aug. 23, 2002, pp. 315-322, XP008036552 ISSN : 0009-7330.
Shi Qx, et al., "Spermine Inhibition of In-Vitro-Fertilizing Ability of Human Spermatozoa . . ." Acta Physiologica Sinica, 1991, Vo. 43, No. 5, pp. 480-488, abstract.
Shi Qx, et al ., Effect of spermine on sperm capacitation of guinea pig in vitro . Arch . Androl., 1992, pp. 33-42, abstract.
Kanwar U., et al, The effect of nifedipine, a calcium channel blocker, on human spermatozoal functions. Contraception, vol. 48, No. 1993, pp. 458-470, abstract.

* cited by examiner

*Primary Examiner* — Sreeni Padmanabhan
*Assistant Examiner* — Samira Jean-Louis
(74) *Attorney, Agent, or Firm* — Stacey J. Farmer, Esq.; Alan Heimlich, Esq.

(57) ABSTRACT

The invention relates to the use of plasma membrane calcium ATPase (PMCA) inhibitors for inhibiting sperm mobility to achieve a contraceptive effect. The invention further relates to contraceptive agents comprising one or more PMCA inhibitors.

6 Claims, 4 Drawing Sheets

FIG. 1

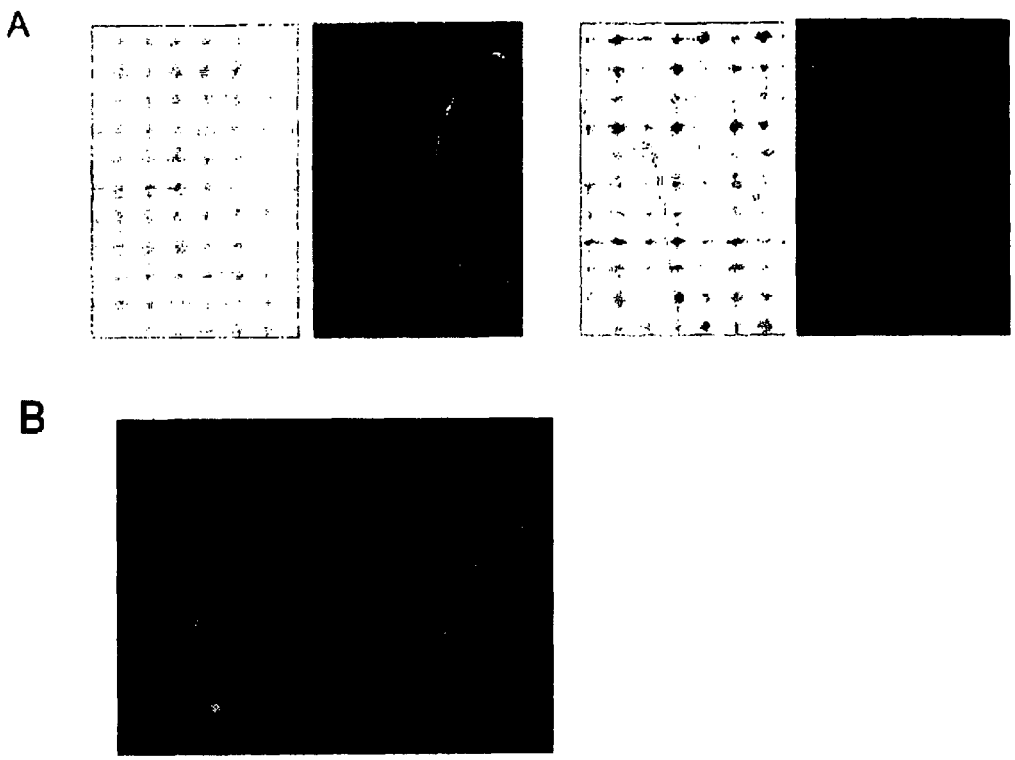

FIGURE 1: Expression of PMCA4 in isolated sperm cells

A: Mouse sperm cells reveal robust expression of PMCA4 in the acrosome and tail (shading, second image). A phase-contrast image of the isolated sperm is provided for comparative purposes. The two right-hand images show the negative control of the secondary antibody alone compared to the phase-contrast photograph of the two sperm cells.

B: As with mouse sperm cells, human sperm cells also express PMCA4 in the acrosome and tail. The staining of the PMCA4 is illustrated here as an example.

FIG. 2
A  Phage insert (~12kb, wild-type allele)
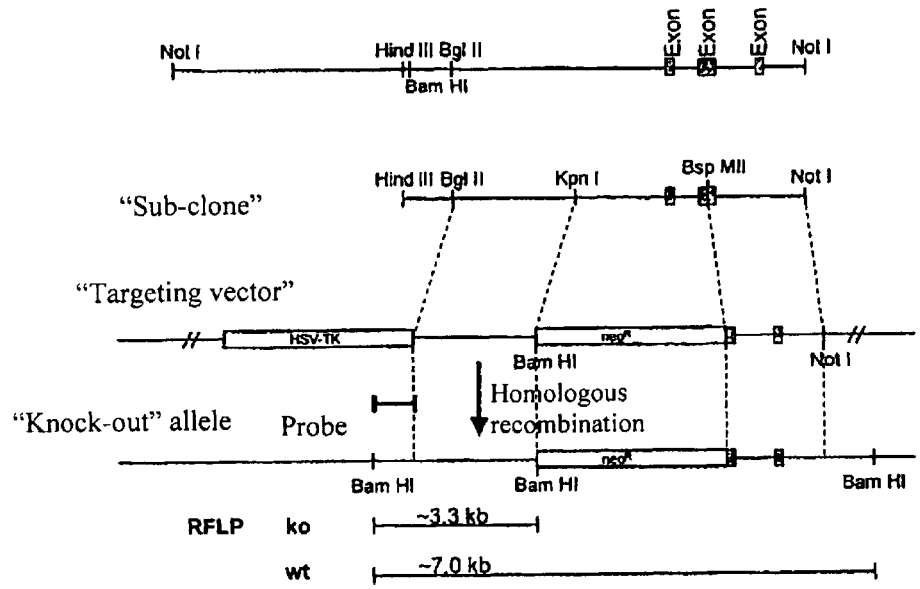
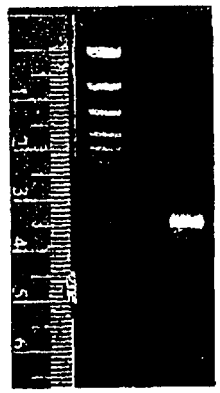
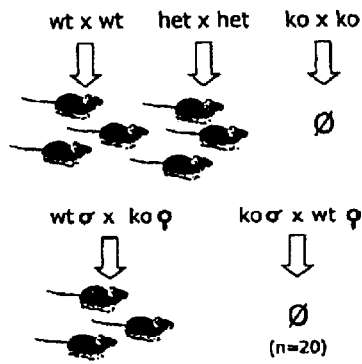
FIG. 2: Infertility in PMCA4-deficient mice.
A: A suitable strategy enabled the PMCA4 gene to be eliminated in the mouse. One complete exon and part of another exon were deleted by using homologous recombination, with the aid of a "targeting vector".

B: The gene manipulation resulted in a complete loss of gene expression in the PMCA4-deficient mice ("ko"), whereas normal mice ("wt") robustly express PMCA4 in sperm. M = Marker to determine the size of the RT-PCR product.

C: The male PMCA4-deficient animals (ko) obtained after genetic manipulation were found to be infertile, regardless of whether they were mated with normal females or with females that were also PMCA4-deficient.

☐ PMCA4

▲ Intra-cellular inhibitor

▦ Extra-cellular inhibitor

METHODS OF DIAGNOSING INFERTILITY BY DETECTING PMCA4 MUTATIONS

The present invention concerns the use of plasma membrane calcium ATPase (PMCA) inhibitors to inhibit sperm mobility in order to achieve a contraceptive effect. The invention further relates to contraceptive agents containing one or more PMCA inhibitors.

THE FIELD OF THE INVENTION

Depending on social, geographic and religious/ethical conditions, the following different contraceptive methods are currently used with varying degrees of reliability: 1) Contraception without the use of mechanical or chemical agents ("Natural Methods"); 2) Contraception by barrier methods, including the use of condoms, occlusive pessaries and vaginal diaphragms; 3) Contraception by substances acting locally, such as spermicides; 4) Hormonal contraception in a woman by the regular ingestion of preparations containing estrogen and/or progesterone that are ingested according to a predetermined plan; 5) Intra-uterine contraception by the use of intra-uterine pessaries, and 6) Surgical sterilization of the man and/or of the woman.

Of the above-described techniques, hormonal contraception is by far the most commonly used method. This method reliably prevents pregnancies and in most cases the contraceptive effect is reversible, i.e. for those wishing to have children, pregnancy occurs in the majority of cases after discontinuing the use of such contraceptive preparations. Unfortunately, however, numerous absolute and relative contra-indications of hormonal contraception are known. The absolute contra-indications of hormonal contraception include thromboses, embolisms, thromo-embolic illnesses, acute and progressive liver diseases, hormone-dependent malignant tumors, bile secretion disorders, sickle-cell anemia, diabetes mellitus including blood vessel damage, hypertension that is difficult to treat, and other clinical conditions. Examples of relative contra-indications include kidney damage, cardiac insufficiency, Raynaud's syndrome, peripheral blood circulation disorders, edemas, difficulties related to nicotine consumption and other related conditions.

Compared to hormonal contraception, "natural contraception" methods are not contra-indicated, however, they are mostly unreliable and are also characterized by an unacceptably high failure rate.

Mechanical methods such as pessaries and sterilization also have considerable disadvantages because of higher complication rates (pessaries) or because they are largely irreversible (sterilization), respectively.

In summary, many known conventional contraceptive methods suffer from considerable disadvantages. A further disadvantage is the fact that up to now the most reliable and commonly used contraceptive method, hormonal contraception, is successfully usable only by a woman, although general public opinion is that contraception is a central responsibility shared by both partners.

Therefore, this invention is based on the task of providing novel non-hormonal contraceptives as preparations to be administered orally or parenterally, or as spermicidal substances, usable both by a woman or a man.

The invention is illustrated by the Figures contained herein.

BRIEF DESCRIPTION OF THE FIGURES

FIG. 1: Expression of PMCA4 in sperm. A. Mouse sperm cells show a strong expression of PMCA4 in the acrosome and in the tail (red color, second image). A phase-contrast image of the isolated sperm is provided for comparative purposes. The two right-hand images show the negative control of the secondary antibody alone compared to the phase-contrast photograph of the two sperm cells. B. As with mouse sperm cells, human sperm cells also express PMCA4 in the acrosome and tail. The staining of the PMCA4 is illustrated here as an example.

FIG. 2: Infertility in PMCA4-deficient mice. A. A suitable strategy enabled the PMCA4 gene to be eliminated in the mouse. One complete exon and part of another exon were deleted by using homologous recombination, with the aid of what is known as a "targeting vector". B. The gene manipulation resulted in a complete loss of gene expression in the PMCA4-deficient mice ("ko"), whereas normal mice ("wt") robustly express PMCA4 in sperm. M=Marker to determine the size of the RT-PCR product. C. The male PMCA4-deficient animals (ko) obtained after genetic manipulation were found to be infertile, regardless of whether they were mated with normal females or with females that were also PMCA4-deficient.

DETAILED DESCRIPTION OF THE INVENTION

Figure 3:
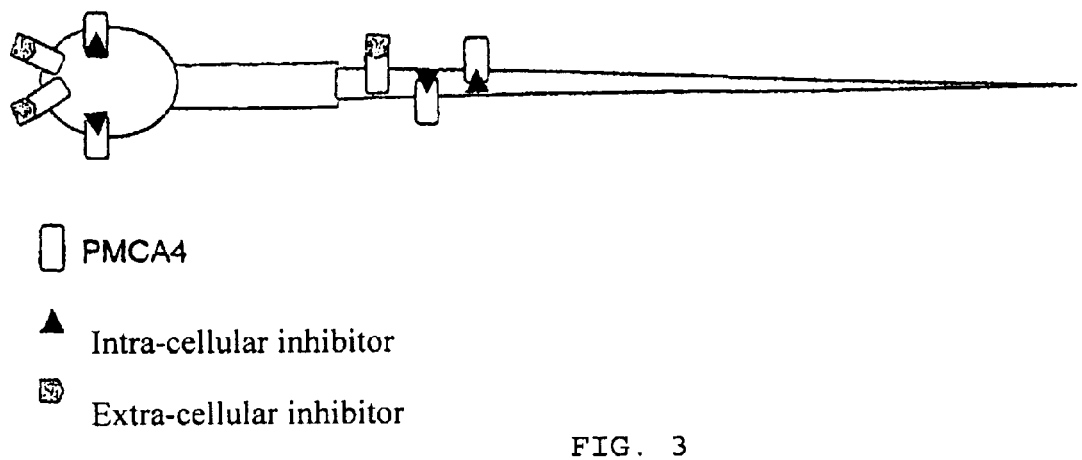
FIG. 3: Diagrammatic illustration of the mode of action of PMCA inhibitors. Inhibitors (shown, gray) that bind to the PMCA (white) in an extra-cellular manner act directly, whereas other substances (black), acting intra-cellularly, must pass through the cell membrane to be able to effectively exert their biological activity.

The present invention concerns the use of plasma membrane calcium ATPase (PMCA) inhibitors to suppress sperm mobility, thus achieving a contraceptive effect.

Furthermore, the invention is aimed at contraceptives containing one or more PMCA inhibitors. These contraceptives may also comprise further conventional contraceptive agents in addition to the PMCA inhibitors.

Another embodiment of the invention concerns a method for contraception whereby a plasma membrane calcium ATPase inhibitor is administered to a mammal.

According to the invention, one or more inhibitors of a plasma membrane calcium ATPase are used to achieve a contraceptive effect. The ATPase enzyme transports calcium out of the cytosol and into the extra-cellular environment. Furthermore, the ATPase enzyme shows homology with other ATPases, including the SERCA ATPase and the sodium/$K^+$ pump. PMCA is encoded by four different genes (PMCA1-4); research studies have demonstrated the existence of several isoforms of PMCA via alternative splicing of the primary gene products. Whereas PMCA gene products 1 and 4 are transcribed in a majority of tissues, PMCA gene products 2 and 3 are expressed in a more tissue-specific manner. The transcription of the PMCA splice variants for these gene products is also tissue-specific. Thus, for example, the β-cells of the pancreas express only the 4b isoforms, whereas the alpha and gamma cells express both the 4a and the 4b isoforms. It was also possible to prove that different splice variants have different affinities for calcium and calmodulin.

The present invention is based on the observation that male mice that are deficient for isoform 4 of murine PMCA (known as "knock-out" mice) are rendered infertile. The animals are otherwise alive and develop normally. Furthermore, no erectile dysfunction is observable in the case of these animals. Surprisingly, however, it was possible to demonstrate that the mobility of the sperm for these PMCA4-"knock-out" mice is restricted to such an extent that fertilization of an egg cell cannot take place, thus the animals are incapable of reproduction. Therefore, there is a highly specific-effect restricted to these sperm cells.

PMCA4 is also expressed in human sperm. The results obtained with the PMCA4-"knock-out" mice suggest that the mobility of human sperm can be restricted using PMCA inhibitors to such an extent that fertilization of the female egg cell is no longer possible.

The specific physiological significance of PMCA for sperm function was previously unknown. Moreover, up to now, there have been no indications that the use of PMCA inhibitors suppresses the mobility of sperm. Therefore, the use of PMCA inhibitors to suppress sperm mobility in order to achieve a contraceptive effect is demonstrated herein for the first time.

Contraceptive activity, i.e. the prevention of the fusion of a sperm with an egg cell, is based on the suppression of the sperm mobility by PMCA inhibitors, which leads to a situation where the sperm can no longer fertilize the egg.

According to the invention, the contraceptive effect is achieved through the use of disclosed PMCA inhibitors.

In a preferred embodiment of the invention, the inhibitor is directed to one of the four isoforms of the plasma membrane calcium ATPase, or PMCA. In this respect, an inhibitor relating to the PMCA4 isoform is especially preferred.

The PMCA inhibitors known from the state of the art can be divided into two main categories, namely, inhibitors that act intra-cellularly and those that act extra-cellularly. According to the invention, the use of either an extra-cellular or an intra-cellular inhibitor, alone or in combination, is described. In this respect, combinations comprising either an intra-cellular or an extra-cellular inhibitors, respectively, as well as combinations comprising an intra-cellular inhibitor together with an extra-cellular inhibitor, can be used.

Known PMCA inhibitors suitable for use in the present invention include 5- (and -6)-carboxyeosindiacetate succinimidyl ester (a cell membrane inhibitor of PMCA), the peptide Caloxin-2A1 which acts on PMCA extra-cellularly, and the poly-cation spermin.

In one embodiment of the invention, 5-(and -6)-carboxyeosindiacetate succinimidyl ester (150347-60-7/2,5-pyrrolidinedione, 1-[[[3',6'-bis(acetyloxy)-2',4',5',7'-tetrabromospiro [isobenzofuran-(3H), 9'-[9H]xanthene]-5(or 6)-yl] carbonyl]oxy]) or derivatives thereof are used as inhibitors of PMCA in sperm.

The corresponding eosin and fluorescein derivatives (Gatto, C. & Milanik, M. A. (1993), *American Journal of Physiology* 264, C1577-1586) are especially preferred derivatives of this inhibitor.

A wide range of eosin, fluorescein, and fluorescin derivatives of the cell membrane passing inhibitor 5-(and -6)-carboxyeosindiacetate succinimidyl ester and their salts already exist, as well as the ester compounds corresponding to 5-(and -6)-carboxyeosindiacetate succinimidyl ester such as, for example, 5-(and -6)-carboxyfluorescein succinimidyl ester (5(6)-FAM). The use of these derivatives is also a preferred embodiment of the invention.

Another embodiment of the invention relates to the use of the PMCA inhibitor, caloxin 2a1 (Holmes, M. E. et al., (2003), *Cell Calcium* 33, 241-245; Chaudary, J. et al., (2001), *Am. J. Physiol. Cell Physiol.* 280, C1027-1030).

Caloxin 2a1, a polypeptide with the amino acid sequence VSNSNWPSFPSSGGG, acts in an extracellular manner with respect to PMCA. It was possible to show in vitro that this oligopeptide binds extra-cellularly to PMCA and has an inhibitory influence on the function of the PMCA.

In a preferred embodiment of the invention, derivatives of caloxin 2a1 are used to inhibit sperm mobility. In this respect, the expression "Variants of Caloxin 2a1" describes chemically modified variants of the peptide, i.e. also including cyclic and all other derivatives. The amino acids comprising the peptide caloxin 2a1 provide a variety of opportunities for chemical modification, e.g. the OH groups of the numerous serine (S) or the amide groups of the two asparagine residues (N) represent suitable starting points for modulating the affinity of the peptide, through which the binding affinity to PMCA4 can also be modulated, thereby influencing and intensifying the inhibitory properties on the PMCA4 on a sperm cell.

Variants of caloxin 2a1 also comprise the insertion, deletion and substitution variants of the amino-acid sequence of the polypeptide. In this respect, insertion variants include amino- and/or carboxyl-terminal fusions as well as insertions of single or multiple amino-acid residues within the sequence. Typically, an insertion variant comprises an addition of 1-14, preferably of 1-7 amino-acids to the amino-acid sequence of caloxin 2a1. Deletion variants are characterized by the removal of one or more amino-acid residues from the caloxin 2a1 oligopeptide. Typically, not more than 2-6 residues are deleted. Substitution variants characterize those variants in which at least one amino-acid of the caloxin 2a1 sequence has been removed and exchanged for a different amino-acid. In general, amino-acids are exchanged for amino-acids with similar properties regarding hydrophobicity, electro-negativity, side-chains and the like. Typically, the variants demonstrate the same properties as unmodified caloxin 2a1.

In another embodiment, the invention is aimed at the use of the PMCA inhibitor spermin (Palacios, J. et al., (2003), *Biochem. Biophys. Acta* 1611, 197-203), a poly-cation, to inhibit sperm mobility. In a preferred embodiment, the invention is aimed at the use of the spermin derivatives, including spermin dihydrate and spermin tetrahydrochloride.

All three starting point substances offer a variety of possibilities for chemical modification in order to modulate and intensify the inhibitory properties relating to the binding affinity of PMCA.

All chemical modifications of the disclosed inhibitors are conceivable, providing that the inhibitory effect of the inhibitor derivatives on the mobility of sperm is still maintained. The mobility of the sperm is determined and described in Example 3.

The PMCA inhibitors can be administered in a variety of ways. In one embodiment of the invention, the inhibitors are administered orally, parenterally, as a coating on mechanical contraceptives, or in the form of a cream, gel or oil. In this regard, the coating of, for example, condoms or other mechanical contraceptives with PMCA inhibitors is especially preferred.

The duration of administration of the PMCA inhibitors is adjustable. One embodiment of the invention is aimed at using the inhibitors for single-use contraception. However, the inhibitors can also be administered repeatedly or chronically. The dosage of the PMCA inhibitors can easily be determined by the person skilled in the art by using methods known in the state of the art.

The inhibitors can be administered to a mammal, preferably a human. In a preferred embodiment, a PMCA inhibitor is administered to a human male. Therefore, the administration of the PMCA inhibitor to the human male for contraception is based on a completely novel principle as described herein. The physiological effect does not intervene in the development of the sperm and therefore it also does not have the side-effects of known hormone preparations for men, such as permanent infertility, "feminization" of the body and other undesirable side-effects.

In another preferred embodiment, a PMCA inhibitor is administered to a woman. When PMCA inhibitors accumulate in the mucus of the uterine cervix or in the uterus, the mobility of the sperm is immediately inhibited as soon as it enters the vaginal area, and therefore, a contraceptive effect is achieved.

Preferably, a PMCA inhibitor is administered both to a man and to a woman, in order to achieve the maximum possible contraceptive effect.

Furthermore, the invention is also aimed at a contraceptive containing a PMCA inhibitor in combination with a pharmaceutically acceptable carrier. In one preferred embodiment, the contraceptive contains not just one PMCA inhibitor but a combination of at least two PMCA inhibitors in combination with a pharmaceutically acceptable carrier.

Known solid or liquid carriers or diluents and the pharmaceutical-technical auxiliary substances that are customary are suitable as a pharmaceutically acceptable carrier at a dosage appropriate to the required type of application.

Contraceptives according to the invention can also be used in combination with conventional contraceptives to yield other contraceptive compositions. In this respect, the conventional contraceptive can be chosen from the group consisting of condoms, diaphragms, contraceptive foam, etc.

Thus, for example, a contraceptive according to the invention can be used to coat a condom in order to obtain a improved conventional contraceptive having improved contraceptive effectiveness. If sperm are brought into contact with contraceptives coated in this manner, the sperm mobility is sharply inhibited and a contraceptive effect is achieved.

Furthermore, the invention is also aimed at the molecular investigation of the PMCA, in particular the gene coding for PMCA. This also comprises the characterization of the various PMCA isoforms and splice variants, as well as the detection of mutations and other modifications, e.g. post-translational changes, for the purposes of diagnosing infertility in men.

Infertility (i.e. childlessness despite a desire for children and normal sexual intercourse) is present in about 15% of all married couples. In approximately 40% of these cases, the cause of the infertility resides in the male partner. The diagnosis of this disorder is still challenging, and in particular possible underlying genetic defects are known only in minimal detail.

Since the PMCA4 isoform is also expressed in human sperm cells, it is reasonable to suppose that in the human organism as well, by analogy with the mouse model, a gene defect affecting PMCA4 also has consequences on male fertility. Therefore, an embodiment of the invention is aimed at diagnostic methods comprising investigating whether male infertility is due to a defective expression of the PMCA mRNA or to a defect in the PMCA4 gene.

The level of expression as well as possible mutations or polymorphisms in the PMCA4 gene and in the genes coding for the other PMCA isoforms can be determined in sperm cells in a ejaculate sample by means of PCR and possibly subsequent sequencing, ELISA, immunohistological detection, Western Blot and PMCA activity determination. In this regard, the determination of PMCA activity is accomplished using known methods. The results from these investigations can form the initial basis for developing suitable therapies in order to treat male infertility.

The following examples are intended to merely illustrate the invention and not to restrict the scope of protection of the invention.

EXAMPLES

Establishing a PMCA4-deficient Mouse Line

Murine lines, whereby the PMCA4 gene was deleted by homologous recombination, were prepared using two different (heterozygously PMCA4-deficient) embryonic stem cell clones. A region of the gene containing Exon 2 together with parts of Exon 3 was deleted (FIG. 2). In addition, multiple stop codons were inserted into all three reading frames by inserting the neomycin-resistant cassette, thus excluding the possible expression of an aberrant protein ("read-through product" or "splicing" variants). A total of 14 male and 6 female chimeras were produced. The male animals were mated with C57B1/6 animals. In the case of several chimeric mice, it was possible to demonstrate the integration of the destroyed PMCA4 allele into the germ line. The resulting male PMCA-deficient animals were infertile, whereas the resulting female mice showed normal fertility.

Expression Analysis of PMCA4 in Murine and Human Sperm

The expression of PMCA4 in murine and human sperm was demonstrated using immunohistochemistry techniques. The results are presented in FIG. 1. Part A of FIG. 1 shows that mouse sperm cells display strong expression of PMCA4 in the acrosome and in the tail (red color, second image). A phase-contrast image of the isolated sperm is provided for comparative purposes. The two right-hand images show the negative controls of the secondary antibody alone compared to the phase-contrast photograph of the two sperm cells. Part B of FIG. 1 shows that human sperm cells, like mouse sperm cells, express PMCA4 both in the acrosome and tail. Only the color schematic representing PMCA4 is illustrated here as an example.

Suppression of Sperm Mobility by PMCA Inhibitors

The inhibition of sperm function, i.e. the inhibition of sperm mobility, was determined as follows:

PMCA4-deficient male mice were sacrificed and the epididymis of each was prepared. These tissues were placed into 2 ml of a sperm preparation medium ("Sperm Preparation Medium" from the MediCult a/s Company, Möllehaven 12, 4040 Jyllinge, Denmark, comprising: Earle's balanced saline solution, sodium pyruvate, synthetic serum substitute, HEPES [hydroxy-ethyl-piperazine ethanesulphonic acid], sodium bicarbonate, human serum albumen; penicillin 50,000 IU/liter and streptomycin 50 mg/liter; Kahn, J. A., *Human Reproduction* 8/9, pages 1414-1419, 1993; Lähteenmäki, A., *Human Reproduction* 10/1, pages 142-147, 1995) and a subsequent incision was made using a sterile scalpel. All functioning sperm were allowed 15 minutes to swim out of the epididymis. The supernatant containing these sperm was removed and mixed with 500 µl each of increasing concentrations of 5- and 6-carboxyeosindiacetate succinimidyl ester (CE). Following this step, the sperm were incubated for 1 hour at 37° C. CE diffuses into the sperm during this time; the ester is hydrolyzed on the intracellular level. Afterwards, the remaining motile sperm were counted in relation to the non-motile ones. The following results were obtained:

TABLE I

| Inhibition of sperm mobility by 5- and 6-CE-succinimidyl ester (CE) | | | | |
|---|---|---|---|---|
| CE concentration (μm) | — | 5 μM | 20 μM | 100 μM |
| Non-motile sperm | 30%[a] | 90% | 95% | 97% |

[a]The percentage of 30% non-motile sperm content in the absence of any inhibitor is typical for preparations derived from the epididymis.

The inhibition of sperm motility was further evaluated automatically using the CASA System 4.2 from the medeaLAB Company, Erlangen, Germany. In this respect, the preparation of the sperm and addition of inhibitor took place as described above. The following three groups were studied using the CASA System:

Group A (untreated, normal sperm, 45 minutes after preparation, 37° C.); Group B (PMCA-deficient sperm, 45 minutes after preparation, 37° C.); Group C (normal sperm, 45 minutes after preparation, 37° C., of which 30 minutes with contacted with 20 μM of the intracellular inhibitor 5- and 6-CE).

The following results were obtained;

Group A: Progressive motility 73%, locally mobile or non-motile 27%, n=254 sperms; Group B: Progressive motility 14%, locally mobile or non-motile 86%, n=198 and Group C: Progressive motility 22%, locally mobile or non-motile 78%, n=217.

For the above automated experimental protocol, the incubation time (compared to manual counting) was shortened (only 30 minutes instead of 1 hour) and the software also recorded non-meaningful objects that were present in the sample, such objects could be readily excluded with manual counting.

The invention claimed is:

1. A method for diagnosing infertility in a human male, comprising:
    obtaining a biological sample from the human male, wherein the biological sample contains one or more sperm cells;
    analyzing the biological sample, wherein
        (i) detecting a mutation or polymorphism in a plasma membrane calcium ATPase 4 (PMCA4) gene encoding PMCA4 in the one or more sperm cells, or
        (ii) detecting a decrease in the expression of PMCA4 in the one or more sperm cells relative to a control sample,
    is diagnostic of infertility; and
    counting a number of non-motile sperm cells relative to motile sperm cells in the biological sample, wherein a number of non-motile sperm cells is greater than 30%.

2. A method for diagnosing infertility in a human male, comprising:
    obtaining a biological sample from the human male, wherein the biological sample contains one or more sperm cells;
    analyzing the biological sample, wherein
        (i) detecting a mutation or polymorphism in a plasma membrane calcium ATPase 4 (PMCA4) gene encoding PMCA4 in the one or more sperm cells, wherein the mutation or polymorphism is detected in exon 2 or exon 3 of the PMCA4 gene or
        (ii) detecting a decrease in the expression of PMCA4 in the one or more sperm cells relative to a control sample,
    is diagnostic of infertility; and counting a number of non-motile sperm cells relative to motile sperm cells in the biological sample, wherein a number of non-motile sperm cells is greater than 30%.

3. The method according to claim 1, wherein the detecting the expression of the PMCA4 is performed using immunohistochemistry, sequencing, ELISA, Western Blot, and PMCA activity determination.

4. The method according to claim 2, wherein the detecting the expression of the PMCA4 is performed using immunohistochemistry, sequencing, ELISA, Western Blot, and PMCA activity determination.

5. The method according to claim 1, wherein detecting the expression of the PMCA4 in the one or more sperm cells is conducted in a sperm cell acrosome and/or tail region.

6. The method according to claim 2, wherein detecting the expression of the PMCA4 in the one or more sperm cells is conducted in a sperm cell acrosome and/or tail region.

* * * * *